United States Patent [19]

Cheng et al.

[11] 4,269,985

[45] May 26, 1981

[54] PROCESS FOR THE PREPARATION OF 2-AMINO-5-NITROTHIAZOLE

[75] Inventors: Dah-Chieh O. Cheng; Kim S. Chamberlin, both of Kingsport, Tenn.

[73] Assignee: Eastman Kodak Company, Rochester, N.Y.

[21] Appl. No.: 173,537

[22] Filed: Jul. 30, 1980

[51] Int. Cl.$^3$ .......................................... C07D 277/38
[52] U.S. Cl. .................................................. 548/191
[58] Field of Search .................. 548/190, 191; 424/270

[56] References Cited

U.S. PATENT DOCUMENTS

| 3,113,947 | 12/1963 | Currie ................................... | 548/191 |
| 3,318,904 | 5/1967 | Schmidt et al. ...................... | 548/191 |
| 3,830,826 | 8/1974 | Strehlke et al. ...................... | 424/270 |

OTHER PUBLICATIONS

Chem. Ber., vol. 98, 3847 (1967).

*Primary Examiner*—Nicholas S. Rizzo
*Attorney, Agent, or Firm*—J. Frederick Thomsen; Daniel B. Reece, III

[57] ABSTRACT

Disclosed is a novel process for the preparation of 2-amino-5-nitrothiazole which comprises the steps of (1) halogenating (chlorinating or brominating) a N,N-dialkyl-2-nitro-etheneamine having the formula $O_2NCH=CHNR^1R^2$ to obtain a compound(s) having the structure

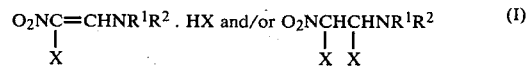 (I)

(2) reacting (I) with thiourea to obtain a compound having the formula

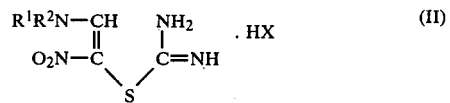 (II)

and (3) treating (II) with water.

10 Claims, No Drawings

PROCESS FOR THE PREPARATION OF 2-AMINO-5-NITROTHIAZOLE

This invention concerns a novel process for the preparation of 2-amino-5-nitrothiazole which avoids hazardous nitration and rearrangement procedures.

The known processes for the preparation of 2-amino-5-nitrothiazole involve first the synthesis of 2-aminothiazole. For example, vinyl acetate can be halogenated to give a 1,2-dihaloethyl acetate which is then reacted with thiourea to yield 2-aminothiazole. The 2-aminothiazole then is treated with a mixture of nitric and sulfuric acids to give 2-nitramino-thiazole which, upon heating, rearranges to 2-amino-5-nitrothiazole. During both the nitration and rearrangement steps, explosions can occur, particularly under conditions employed in commercial scale operations.

According to the process of this invention, 5-nitro-2-aminothiazole is obtained without the use of 5-aminothiazole which thus avoids the necessity of using hazardous nitration and rearrangement procedures. The process involves the steps of (1) halogenating (chlorinating or brominating) a N,N-dialkyl-2-nitroetheneamine having the formula $O_2NCH{=}CHNR^1R^2$ to obtain a compound having the structure

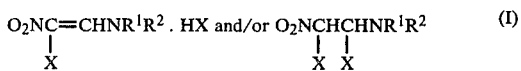
(I)

(2) reacting (I) with thiourea to obtain a compound having the formula

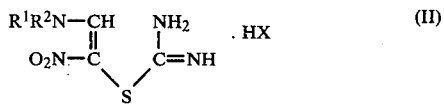
(II)

and (3) treating (II) with water or aqueous base to obtain 5-nitro-2-aminothiazole. In the above formulas $R^1$ and $R^2$ are alkyl of up to about 4 carbon atoms or in combination they can be pentamethylene or 3-oxapentamethylene and X is Cl or Br.

The starting material, the N,N-dialkyl-2-nitroetheneamine, can be prepared according to known procedures such as the one described in Chem. Ber., 98, 3847 (1967). Each of the alkyl groups on the amine starting material preferably is methyl since the amine can most economically be derived from dimethylformamide.

The first step of the process of this invention is not in itself unique but involves a conventional halogenation reaction using an inert organic solvent and a halogenating agent at a temperature commonly used in such reactions. Typical of the solvents which are inert to both of the reactants are alkanols containing up to about 4 carbon atoms, alkanoic acids containing 2 to about 4 carbon atoms, tetrahydrofuran, dimethylformamide and various halogenated hydrocarbons such as methylene chloride, ethylene dichloride, carbon tetrachloride and mono-, di- and tri-chlorobenzene. The lower alkanols are the preferred solvents. Examples of the halogenating agents which may be used include bromine, chlorine, sulfuryl chloride and sulfuryl bromide. The mole ratio of amine reactant to halogenating agent should be about 1:1 to give maximum yields of the desired monohalogenated compound. The halogenation temperature should be less than 25° C. and preferably in the range of about −5° to 20° C. Due to analytical incapabilities the exact composition of the halogenated product is not known. However, when the amine reactant to halogenating agent mole ratio is about 1:1 or more the halogenated product is believed to have either or possibly both of the structures described hereinabove.

The product of the first step having formula (I) normally is not isolated but is allowed to remain in the resulting reaction mixture for reaction with thiourea. The amount of thiourea used in the second step obviously should be sufficient to react with the halogen compound of formula (I). Since the halogenation is essentially quantitative, at least 1 mole of thiourea is used per mole of the amine starting material. It is preferred to use an excess, e.g., up to 50 mole percent, of thiourea to insure complete reaction of the formula (I) compound. Usually, no additional inert solvent is used in the second step although one or more additional solvents could be present if desired. The reaction can be conveniently carried out at room temperature although temperatures slightly higher or as low as 0° C. can be used.

The second step of my novel process is unusual in that it would have been expected that the product obtained therefrom would have been the closed ring compound, 2-amino-5-nitrothiazole. However, the product which precipitates is the acyclic compound having formula (II).

The third step of our novel process involves treating the formula (II) compound with water to effect ring-closure and thereby obtain 2-amino-5-nitrothiazole. If desired, the water may contain a base such as ammonium hydroxide or the hydroxides and carbonates of the alkali metals. The third step can be performed effectively at room temperature although temperatures slightly higher or as low as 0° C. can be used when it is convenient to do so. Normally the salt of formula (II) dissolves in the water and then the 2-amino-5-thiazole quickly precipitates. The amount of water that is required usually will be determined by the facilities employed. Weight ratios of 1–10 parts per part of the salt will give satisfactory results while weight ratios of about 2–3:1 are preferred. In the third step, the salt of formula (II) employed may have been isolated in the second step or the water may be added to the reaction mixture resulting from the second step.

The process of my invention will be further illustrated by the following examples.

EXAMPLE 1

To a stirred mixture of 3.5 g (0.03 mol) of N,N-dimethyl-2-nitroetheneamine in 25 ml of ethanol chilled at 0°–5° C. under nitrogen was added 4.8 g (0.03 mol) of bromine dropwise so that the mixture stayed below 10° C. (30 minutes). Upon completion of bromine addition a solution was observed. To the resulting solution of the compound having the structure $O_2N(Br)C{=}CHN(CH_3)_2 \cdot HBr$ was added 3 g (0.039 mol) of thiourea at ice temperature. The cooling bath was removed and the thiourea first dissolved. In 15 minutes a white precipitate appeared. This mixture was allowed to stir at room temperature for one hour, then again cooled to ice temperature. The precipitate was filtered, washed with a small amount of cold ethanol and then dried under a dry nitrogen atmosphere to give 8.05 g (99% yield) of product as a sandy well-packed solid. Mp. 130° C. (decomposed). The product had the formula

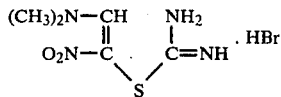

EXAMPLE 2

To 10 ml of water was added 2.71 g (0.01 mol) of the product of Example 1. The salt dissolved very quickly and in 5 minutes a yellow solid started to precipitate. The mixture was stirred an additional one hour and then the precipitate was filtered off, washed with water and then dried to give 1.2 g (82.8%) of 5-nitro-2-aminothiazole; m.p. 198° C. (decomposed).

EXAMPLE 3

To a stirred mixture of 3.5 g of N,N-dimethyl-2-nitroetheneamine in 25 ml of acetic acid cooled to 17° C. was added 4.8 g bromine at such a rate the reaction temperature did not exceed 25° C. During bromination an orange solid was formed. After stirring the resulting slurry for 10 minutes, 3.0 g thiourea was added and the reaction mixture exothermed to 32° C. A yellow solid formed. The mixture was stirred for 1 hour and then was diluted with 25 ml of water. This mixture and an approximately equal volume of 29% ammonium hydroxide were added simultaneously to 25 ml of acetic acid at such rates that the pH remained between 4 and 5 and the temperature did not exceed 30° C. After all of the reaction mixture had been added the pH was adjusted to 7 with 29% ammonium hydroxide. The product was then filtered off, washed with water and dried to give 2.7 g (62% yield, 92.9% assay) of 2-amino-5-nitrothiazole.

EXAMPLE 4

Dimethyl sulfate (126 g, 1.0 mol) was added dropwise over one-half hour to dimethylformamide (73 g, 1.0 mol) heated to 60° C. The solution was stirred at 60° C. for two hours after completion of addition before cooling to room temperature. Nitromethane (61 g, 1.0 mol) was added and mixed thoroughly. This mixture was added dropwise over one hour to a slurry of sodium acetate (82 g, 1 mol) in one liter of isopropanol at 50° C. The yellow slurry was stirred at 50° C. for two hours after completion of the addition. To this slurry, cooled to 5° C., was added bromine (128 g, 0.8 mol) at such a rate that the temperature did not exceed 10° C. After the resulting yellow solution was stirred for one-half hour at 5° C., thiourea (61 g, 0.8 mol) was added and the cooling means were removed. The mixture exothermed to 30° C., was stirred at room temperature for one hour and then was cooled to 5° C. The isopropanol was removed by using a filter leg and 500 ml isopropanol was added to the remaining solids, stirred and then removed. Water (500 ml) was added to the white solid and, upon stirring, a yellow solution was immediately obtained. The agitation was stopped and, upon cooling to 5° C., yellow needles precipitated. The 2-amino-5-nitrothiazole product was filtered off, washed with water and dried. The yield was 32% based on nitromethane and 42% based on bromine.

The invention has been described in detail with particular reference to certain preferred embodiments thereof, but it will be understood that variations and modifications can be effected within the spirit and scope of the invention.

We claim:

1. Process for the preparation of 2-amino-5-nitrothiazole which comprises the steps of:
   A. Halogenating a compound having the formula $O_2NCH=CHNR^1R^2$ to obtain a compound having the formula $O_2N(X)C=CHNR^1R^2.HX$ and/or $O_2N(X)CHCH(X)NR^1R^2$;
   B. Reacting the product of A with thiourea to obtain a compound having the formula

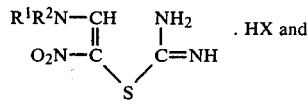

C. Contacting the product of B with water; wherein $R^1$ and $R^2$ are each alkyl containing up to about 4 carbon atoms or in combination they can be pentamethylene or 3-oxapentamethylene and X is Cl or Br.

2. Process according to claim 1 which comprises the steps of:
   A. Chlorinating or brominating a compound having the formula $O_2NCH=CHNR^1R^2$ in the presence of an alkanol or an alkanoic acid having up to about 4 carbon atoms to obtain a compound having the formula $O_2N(X)C=CHNR^1R^2.HX$ and/or $O_2N(X)CHCH(X)NR^1R^2$;
   B. Adding thiourea to the solution resulting from Step A to obtain a compound having the formula

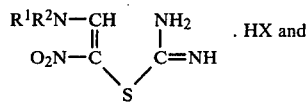

C. Contacting the product of Step B with water.

3. Process according to either of claims 1 or 2 wherein the halogenating agent is $Cl_2$, $Br_2$ or $SO_2Cl_2$.

4. Process according to claim 2 which comprises the steps of:
   A. Treating a compound having the formula $O_2NCH=CHN(CH_3)_2$ with $Br_2$ or $Cl_2$ in the presence of an alkanol having up to about 4 carbon atoms to obtain a compound having the formula $O_2N(X)C=CHN(CH_3)_2$ and/or $O_2N((X)CHCH(X)N(CH_3)_2$;
   B. Adding thiourea to the solution resulting from Step A to obtain a compound having the formula

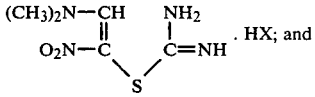

C. Contacting the product of Step B with water.

5. Process according to claim 4 in which $Br_2$ is employed in Step A and the product of Step B is isolated.

6. Process which comprises the reaction of a compound having the formula $O_2N(X)C=CHNR^1R^2.HX$ and/or $O_2N(X)CHCH(X)NR^1R^2$ with thiourea to obtain a compound having the formula $$\begin{array}{c} R^1R^2NCH \quad NH_2 \\ \parallel \quad\quad | \\ O_2N-C \quad\quad C=NH \\ \diagdown S \diagup \end{array} \cdot HX$$

wherein $R^1$ and $R^2$ each is alkyl containing up to 4 carbon atoms and X is Cl or Br.

7. Process according to claim 6 which comprises adding thiourea to a solution of a compound having the formula $O_2N(Br)C=CHN(CH_3)_2$ and/or $O_2N(Br)CHCH(Br)N(CH_3)_2$ to obtain a compound having the formula $$\begin{array}{c} (CH_3)_2N-CH \quad NH_2 \\ \parallel \quad\quad | \\ O_2N-C \quad\quad C=NH \\ \diagdown S \diagup \end{array} \cdot HBr$$

8. Process for the preparation of 2-amino-5-nitrothiazole which comprises the steps of:
   A. Treating an amine having the formula $O_2NCH=CHNR^1R^2$ with a halogenating agent to obtain a halogenated compound;
   B. Reacting the product of A with thiourea to obtain a compound having the formula $$\begin{array}{c} R^1R^2N-CH \quad NH_2 \\ \parallel \quad\quad | \\ O_2N-C \quad\quad C=NH \\ \diagdown S \diagup \end{array} \cdot HX \text{ and}$$

C. Contacting the product of B with water; wherein $R^1$ and $R^2$ are each alkyl containing up to about 4 carbon atoms or in combination they can be pentamethylene or 3-oxapentamethylene and the halogenating agent is bromine, chlorine, sulfuryl chloride or sulfuryl bromide and the mole ratio of amine to halogenating agent is about 1:1.

9. Process according to claim 8 which comprises the steps of:
   A. Treating an amine having the formula $O_2NCH=CHNR^1R^2$ with a halogenating agent in the presence of an alkanol or an alkanoic acid having up to about 4 carbon atoms to obtain a solution of a halogenated compound;
   B. Adding thiourea to the solution resulting from Step A to obtain a compound having the formula $$\begin{array}{c} R^1R^2N-CH \quad NH_2 \\ \parallel \quad\quad | \\ O_2N-C \quad\quad C=NH \\ \diagdown S \diagup \end{array} \cdot HX \text{ and}$$

C. Contacting the product of Step B with water.

10. Process according to claim 9 which comprises the steps of:
   A. Treating an amine having the formula $O_2NCH=CHN(CH_3)_2$ with $Br_2$ or $Cl_2$ in the presence of an alkanol having up to about 4 carbon atoms to obtain a halogenated compound;
   B. Adding thiourea to the solution resulting from Step A to obtain a compound having the formula $$\begin{array}{c} (CH_3)_2N-CH \quad NH_2 \\ \parallel \quad\quad | \\ O_2N-C \quad\quad C=NH \\ \diagdown S \diagup \end{array} \cdot HX; \text{ and}$$

C. Contacting the product of Step B with water.

* * * * *